United States Patent
Landers et al.

(10) Patent No.: US 10,656,146 B2
(45) Date of Patent: May 19, 2020

(54) DETECTION OF POLYMERIC ANALYTES (75) Inventors: James P. Landers, Charlottesville, VA (US); Daniel C. Leslie, Brookline, MA (US)

(73) Assignee: University of Virginia Patent Foundation, Charlottesville, VA (US)

(*) Notice: Subject to any disclaimer, the term of this patent is extended or adjusted under 35 U.S.C. 154(b) by 588 days.

(21) Appl. No.: 12/879,810

(22) Filed: Sep. 10, 2010

(65) Prior Publication Data
US 2011/0070660 A1    Mar. 24, 2011

Related U.S. Application Data (63) Continuation of application No. PCT/US2009/036983, filed on Mar. 12, 2009.

(60) Provisional application No. 61/035,923, filed on Mar. 12, 2008.

(51) Int. Cl.
*G01N 33/543* (2006.01)
*G01R 33/12* (2006.01)

(52) U.S. Cl.
CPC ... *G01N 33/54326* (2013.01); *G01R 33/1269* (2013.01); *B01J 2219/005* (2013.01)

(58) Field of Classification Search
CPC ........... G01R 33/1269; G01N 33/54326; B01J 2219/005
USPC .................................. 436/518, 526
See application file for complete search history.

(56) References Cited

U.S. PATENT DOCUMENTS

| | | | |
|---|---|---|---|
| 5,447,842 A | 9/1995 | Simons et al. | |
| 5,523,231 A | 6/1996 | Reeve | |
| 5,601,991 A | 2/1997 | Oberhardt | |
| 5,677,133 A * | 10/1997 | Oberhardt | 435/7.1 |
| 6,361,944 B1 | 3/2002 | Mirkin et al. | |
| 6,500,343 B2 | 12/2002 | Siddiqi | |
| 6,673,631 B1 | 1/2004 | Tereba et al. | |

(Continued)

FOREIGN PATENT DOCUMENTS

| | | |
|---|---|---|
| EP | 1712622 A1 | 10/2006 |
| EP | 2265942 | 10/2017 |

(Continued)

OTHER PUBLICATIONS

Vuppu et al. "Phase Sensitive enhancement for biochemical detection using rotating paramagnetic particle chains". Journal of Applied Physics 96, No. 11, Dec. 2004, p. 6831-6838.*

(Continued)

*Primary Examiner* — Rebecca L Martinez (74) *Attorney, Agent, or Firm* — Schwegman Lundberg & Woessner, P.A.

(57) ABSTRACT

The present invention relates to methods for detecting polymeric analytes, especially biopolymers, and sensors for detecting the polymeric analytes. The present invention uses magnetic beads in a rotating magnetic field to provide a visual detection of the presence of a polymeric analyte, such as nucleic acids, lipids, polysaccharides, proteins, etc. When a polymeric analyte binds to the magnetic beads, application of a rotating magnetic field to the beads results in unique pinwheel formations. Without the presence of the polymeric analyte, the movement of the magnetic beads induced by the rotating magnetic field differs significantly from the pinwheel formations. The pinwheel, therefore, is used to detect the presence of polymeric analytes.

23 Claims, 11 Drawing Sheets

(56) References Cited

U.S. PATENT DOCUMENTS

| | | |
|---|---|---|
| 9,415,392 B2 | 8/2016 | Ismagilov et al. |
| 2001/0007312 A1* | 7/2001 | Siddiqi .................... 210/695 |
| 2002/0028519 A1 | 3/2002 | Yguerabide et al. |
| 2002/0081714 A1 | 6/2002 | Jain et al. |
| 2002/0164825 A1 | 11/2002 | Chen |
| 2003/0096424 A1* | 5/2003 | Mao et al. .................... 436/169 |
| 2003/0215825 A1 | 11/2003 | Tong |
| 2004/0005613 A1 | 1/2004 | Norton |
| 2004/0058458 A1* | 3/2004 | Anker et al. .................. 436/526 |
| 2004/0086930 A1* | 5/2004 | Tereba et al. .................... 435/6 |
| 2004/0126902 A1* | 7/2004 | Nishiya et al. ............... 436/526 |
| 2005/0170418 A1 | 8/2005 | Moreland et al. |
| 2005/0250096 A1 | 11/2005 | Wheeler et al. |
| 2006/0129327 A1 | 6/2006 | Kim et al. |
| 2006/0252031 A1 | 11/2006 | Abbott et al. |
| 2007/0141583 A1 | 6/2007 | Li et al. |
| 2008/0050721 A1 | 2/2008 | Radka et al. |
| 2012/0149587 A1 | 6/2012 | Landers et al. |
| 2013/0084565 A1 | 4/2013 | Landers et al. |
| 2013/0203045 A1 | 8/2013 | Landers et al. |

FOREIGN PATENT DOCUMENTS

| | | |
|---|---|---|
| KR | 1020060094416 A | 8/2006 |
| WO | WO-1994019690 A1 | 9/1994 |
| WO | WO-2003045310 A2 | 6/2003 |
| WO | WO-03/096014 A2 | 11/2003 |
| WO | WO-2003096014 A2 | 11/2003 |
| WO | WO-2005019836 A2 | 3/2005 |
| WO | WO-2005079995 A1 | 9/2005 |
| WO | WO-2005111596 A1 | 11/2005 |
| WO | WO-2006031920 A2 | 3/2006 |
| WO | WO-2007004687 A1 | 1/2007 |
| WO | WO-2008073624 A2 | 6/2008 |
| WO | WO-2009114709 A2 | 9/2009 |
| WO | WO-2009114709 A3 | 9/2009 |
| WO | WO-2011150226 A1 | 12/2011 |
| WO | WO-2011150226 A9 | 12/2011 |
| WO | WO-2012027747 A2 | 3/2012 |
| WO | WO-2012151268 A1 | 11/2012 |
| WO | WO-2012151289 A2 | 11/2012 |
| WO | WO-2012151289 A3 | 11/2012 |

OTHER PUBLICATIONS

Vuppu et al. ("Phase sensitive enhancement for biochemical detection using rotating paramagnetic particle chains" J. Appl. Phys., vol. 96, No. 11, Dec. 1, 2004, pp. 6831).*
"U.S. Appl. No. 13/116,659, Non Final Office Action dated Jul. 13, 2012", 13 pgs.
"International Application Serial No. PCT/US2011/038166, Search Report dated Sep. 21, 2011", 6 pgs.
"International Application Serial No. PCT/US2011/038166, Written Opinion dated Sep. 21, 2011", 6 pgs.
"International Application Serial No. PCT/US2012/036105, Search Report dated Aug. 16, 2012", 4 pgs.
"International Application Serial No. PCT/US2012/036105, Written Opinion dated Aug. 16, 2012", 6 pgs.
"International Application Serial No. PCT/US2012/036139, Invitation to Pay Additional Fees dated Sep. 11, 2012", 39 pgs.
Crawford, A M, et al., "Patterned Magnetic Bar Array for High-Throughput DNA Detection", IEEE Transactions on Amagnetics, IEEE Service Center. vol. 40, No. 4, (Jul. 1, 2004), 3 pgs.
Haukanes, B I, et al., "Application of Magnetic Beads in BioAssays", Bio/Technology, Nature Publishing Co. vol. 11 No. 1, (Jan. 1, 1993), 4 pgs.
Morozov, V N, et al., "Active bead-linked immunoassay on protein microarrays", Analytica Chimica Acta. vol. 564, No. 1, (Mar. 30, 2006), 13 pgs.
Moser, C, et al., "Microsphere sedimentation arrays for multiplexed bioanalytics", Analytica Chimica Acta. vol. 558 No. 1-2, (Feb. 3, 2006), 8 pgs.

Rosi, N. L., et al., "Nanostructures in Biodiagnostics", Chemical Reviews, American Chemical Society, vol. 105, No. 4, (Mar. 2004), 1547-1562.
Wang, J, et al., "Magnetically-Induced Solid-State Electrochemical Detection of DNA Hybridization", Journal of the American Chemical Society, ACS Publications. vol. 124 No. 16, (Jan. 1, 2002), 2 pgs.
U.S. Appl. No. 13/505,406, filed May 1, 2012, Versatile, Visible Method for Detecting Polymeric Analytes.
U.S. Appl. No. 13/699,983, filed Nov. 26, 2012, Method for Detecting Nucleic Acids Based on Aggregate Formation.
U.S. Appl. No. 13/116,659, filed May 26, 2011, Method for Detecting Nucleated Cells.
"European Application Serial No. 09720315.2, Amended Claims Response Filed Nov. 17, 2010", 8 pgs.
"European Application Serial No. 09720315.2,Extended European Search Report dated Mar. 25, 2011", 8 Pgs.
"International Application Serial No. PCT/US2009/036983, International Preliminary Report on Patentability dated Sep. 14, 2010", 5 pgs.
"International Application Serial No. PCT/US2010/002883, Search Report dated Jan. 26, 2011", 7 pgs.
"International Application Serial No. PCT/US2010/002883,Written Opinion dated Jan. 26, 2011", 7 pgs.
Bienvenue, J. M, et al., "An integrated microfluidic device for DNA purification and PCR amplification of STR fragments", Forensic Sci Int Genet., 4(3), (Apr. 2010), 178-86.
Duarte, G. R, et al., "Characterization of dynamic solid phase DNA extraction from blood with magnetically controlled silica beads", Analyst, 135(3), (Mar. 2010), 531-7.
Hagan, K. A, et al., "Chitosan-coated silica as a solid phase for RNA purification in a microfluidic device", Anal Chem., 81(13), (Jul. 1, 2009), 5249-56.
Price, C. W, et al., "Nucleic acid extraction techniques and application to the microchip", Lab Chip., 9(17), (Sep. 7, 2009), 2484-94.
"International Application Serial No. PCT/US2009/036983, International Search Report dated Oct. 1, 2009", 5 pgs.
"International Application Serial No. PCT/US2009/036983, Written Opinion dated Oct. 1, 2009", 4 pgs.
"U.S. Appl. No. 13/116,659, Final Office Action dated Mar. 13, 2013", 16 pgs.
"U.S. Appl. No. 13/116,659, Response filed Dec. 13, 2012 to Non Final Office Action dated Jul. 13, 2012", 9 pgs.
"U.S. Appl. No. 13/505,406, Preliminary Amendment dated May 1, 2012", 7 pgs.
"U.S. Appl. No. 13/505,406, Supplemental Preliminary Amendment dated Nov. 16, 2012", 6 pgs.
"U.S. Appl. No. 13/699,983, Preliminary Amendment dated Nov. 26, 2012", 6 pgs.
"U.S. Appl. No. 13/699,983, Supplemental Preliminary Amendment filed Apr. 17, 2013", 7 pgs.
"International Application Serial No. PCT/US2011/038166, Preliminary Report on Patentability dated Dec. 6, 2012", 8 pgs.
"International Application Serial No. PCT/US2012/036139, International Search Report dated Jan. 17, 2013", 8 pgs.
"International Application Serial No. PCT/US2012/036139, Written Opinion dated Jan. 17, 2013", 10 pgs.
"U.S. Appl. No. 13/116,659, Final Office Action dated Oct. 15, 2013", 9 pgs.
"U.S. Appl. No. 13/116,659, Response filed Apr. 2, 2014 to Final Office Action dated Oct. 15, 2013", 7 pgs.
"U.S. Appl. No. 13/116,659, Response filed Jul. 10, 2013 to Final Office Action dated Mar. 13, 2013", 7 pgs.
"U.S. Appl. No. 13/505,406, Response filed Mar. 25, 2014 to Restriction Requirement dated Nov. 25, 2013", 7 pgs.
"U.S. Appl. No. 13/505,406, Restriction Requirement dated Nov. 25, 2013", 8 pgs.
"Australian Serial No. 2009223122, First Examiner Report dated Dec. 5, 2013", 4 pgs.
"International Application Serial No. PCT/US2012/036105, International Preliminary Report on Patentability dated Nov. 14, 2013", 8 pgs.

(56) References Cited

OTHER PUBLICATIONS

"International Application Serial No. PCT/US2012/036139, International Preliminary Report on Patentability dated Nov. 14, 2013", 12 pgs.

"Korean Application Serial No. 10-2010-7022805, Amendment filed Mar. 12, 2014", With English Claims, 11 pgs.

Australian Serial No. 2009223122, Response filed Oct. 21, 2014 to First Examiner Report dated Dec. 5, 2013, 16 pgs.

"Korean Application Serial No. 10-2010-7022805, Notice of Preliminary Rejection dated Apr. 2, 2015", (w/ English Summary), 7 pgs.

"U.S. Appl. No. 13/116,659, Non Final Office Action dated Dec. 15, 2014", 14 pgs.

"U.S. Appl. No. 13/505,406, Final Office Action dated Dec. 10, 2014", 17 pgs.

"U.S. Appl. No. 13/505,406, Non Final Office Action dated Jun. 3, 2014", 14 pgs.

"U.S. Appl. No. 13/505,406, Response filed Oct. 3, 2014 to Non Final Office Action dated Jun. 3, 2014", 11 pgs.

"U.S. Appl. No. 13/699,983, Non Final Office Action dated Aug. 14, 2015", 10 pgs.

"U.S. Appl. No. 13/699,983, Response filed Feb. 16, 2016 to Non Final Office Action dated Aug. 14, 2015", 8 pgs.

El-Boubbou, K., et al., "Magnetic Glyco-nanoparticles: A Unique Tool for ZRF Rapid Pathogen Detection, Decontamination, and Strain Differentiation", J. Am. Chem. Soc., 129, (2007), 13392-13393.

Gu, et al., "", Chem. Commun., (2006), 941-949.

Nam, et al., "", Science, vol. 301, (2003), 1884-1887.

Yeung, et al., "", Biosensors and Bioelectronics, vol. 21, (2011), 989-997.

"Indian Application Serial No. 7208/DELNP/2010, Hearing Notice dated Apr. 10, 2018", 2 pgs.

"U.S. Appl. No. 13/699,983, Final Office Action dated Jul. 15, 2016", 12 pgs.

"European Application Serial No. 09720315.2, Communication Pursuant to Article 94(3) EPC dated Sep. 7, 2016", 4 pgs.

Schmidt, et al., "", Nature Methods, (2007), 1051-1057 pgs.

Wang, et al., "", JACS 2002, 124, (2002), 4208-4209 pgs.

"U.S. Appl. No. 13/699,983, Final Office Action dated Jan. 18, 2018", 13 pgs.

"U.S. Appl. No. 13/699,983, Non Final Office Action dated Mar. 23, 2017", 10 pgs.

"U.S. Appl. No. 13/699,983, Respons filed Jan. 16, 2017 to Final Office Action dated Jul. 15, 2017", 9 pgs.

"U.S. Appl. No. 13/699,983, Response filed Sep. 25, 2017 to Non Final Office Action dated Mar. 23, 2017", 8 pgs.

"European Application Serial No. 09720315.2, Response filed Jan. 7, 2017 to Communication Pursuant to Article 94(3) EPC dated Sep. 7, 2016", 10 pgs.

"Indian Application Serial No. 7208/DELNP/2010, First Examiner Report dated Feb. 10, 2017", 9 pgs.

"Indian Application Serial No. 7208/DELNP/2010, Response filed Nov. 9, 2017 to First Examiner Report dated Feb. 10, 2017", 12 pgs.

"Korean Application Serial No. 10-2012-7014224, Final Office Action dated Dec. 11, 2017", W/English Translation, 5 pgs.

"Korean Application Serial No. 10-2012-7014224, Office Action dated Feb. 14, 2016", With English Translation, 16 pgs.

"Korean Application Serial No. 10-2012-7014224, Response filed Aug. 14, 2017 to Office Action dated Feb. 14, 2016", W/English Claims, 20 pgs.

Gijs, et al., "Microfluid Nanofluid", (2004), 22-40.

Goodridge, et al., "", Appl and Environ Microbiol, 65(4), (1999), 1397-1404.

\* cited by examiner

30ng hDNA
4 μL MAGNETIC BEADS

*FIG. 10A*

15ng DNA
2 μL MAGNETIC BEADS

*FIG. 10B*

3ng DNA
1 μL MAGNETIC BEADS

*FIG. 10C*

300pg DNA
0.2 μL MAGNETIC BEADS

*FIG. 10D*

30pg DNA
0.2 μL MAGNETIC BEADS

DETECTION OF POLYMERIC ANALYTES

CLAIM OF PRIORITY

This application is a continuation under 35 U.S.C. 111(a) of International Patent Application Serial No. PCT/US2009/036983, filed Mar. 12, 2009, and published on Sep. 17, 2009 as WO 2009/114709 A2, which application claimed benefit of priority under 35 U.S.C. 119(e) to U.S. Provisional Application Ser. No. 61/035,923 filed Mar. 12, 2008, the contents of which are incorporated herein by reference in their entirety, and the benefit of priority of each of which is claimed herein.

FIELD OF THE INVENTION

The present invention relates to methods for detecting polymeric analytes, especially biopolymers, and sensors for detecting the polymeric analytes. In particular, the present invention relates to the formation of unique pinwheel formations when polymeric analytes bind to magnetic beads and exposed to a rotating magnetic field.

BACKGROUND OF THE INVENTION

Polymeric analytes can be detected using current methods such as chromatograph, electrophoresis, binding assays, spectrophotometry, etc. For example with nucleic acids, DNA concentration has been detected spectrometrically by measuring absorbance of a sample at 260 nm. This method gives reliable detection and quantification at relatively high concentration of DNA; however, it suffers from poor sensitivity at low concentrations.

Other methods for DNA detection include binding DNA to a fluorescence dye and detecting the fluorescence using a fluorometer. Examples of such a dye are PicoGreen®, which is commercially available through Invitrogen (Carlsbad, Calif.), and dyes disclosed in U.S. Pat. Nos. 6,664,047, 5,582,977, and 5,321,130. Although highly sensitive, the fluorometer methods are generally cumbersome, requiring reagent preparation and handling and special fluorometer for exciting and measuring fluoro-emission.

Likewise, proteins can be detected spectrophotometrically by measuring absorbance at 280 nm. Another method for protein detection is the Lowry assay. This method is based on the reduction phosphomolybdic-tungstic mixed acid chromogen in the Folin-Ciocalteu's phenol reagent by protein resulting in an absorbance maximum at 750 nm. Other methods to detect protein include the Bradford assay and the Biuret assay. These assays suffer from either low sensitivity or intensive laboratory preparation and procedure.

The presence of carbohydrates can also be determined spectrophotometrically by detecting their reducing ends using dinitrosalicylic acid. This involves heating a sample in the presence of dinitrosalicylic acid in boiling water the measuring the absorbance at 540 nm. Again, this method suffers from low sensitivity and intensive laboratory preparation and procedure.

Generally, detection of analytes in a microfluidic apparatus requires 1) high sensitivity because the analyte concentration is generally low; and 2) that the method be simple, requiring minimum number of reagents and fluid handling. Therefore, especially in the microfluidic arena, there remains a need for a simple, fast, and sensitive method and apparatus for detecting nucleic acids.

SUMMARY OF THE INVENTION

Efficient molecular analysis usually requires detecting the presence of an analyte in a very small sample at very low concentration. The use of an external magnetic fields in microdevices to implement magnetic beads control has previously been disclosed, e.g. by U.S. Pat. Nos. 7,452,726; 6,664,104; 6,632,655; and 6,344,326; which are incorporated herein by reference. The present invention, however, uses magnetic beads in a rotating magnetic field to provide a visual detection of the presence of a polymeric analyte, such as nucleic acids, lipids, polysaccharides, proteins, etc. This method arises from the observation that when a polymeric analyte binds to the magnetic beads, application of a rotating magnetic field to the beads results in unique pinwheel formations. Without the presence of the polymeric analyte, the movement of the magnetic beads induced by the rotating magnetic field differs significantly from the pinwheel formations. As such, the pinwheel formation is specific to the presence of the binding between the polymeric analyte and the magnetic beads, and therefore, can be used to detect the presence of the analyte.

An object of the present invention relates to a method for detecting the presence of polymeric analyte in a sample by contacting the sample with a magnetic bead and exposing magnetic beads to a rotating magnetic field. The presence of pinwheel formations indicates the presence of the bound polymeric analyte. Preferably, the magnetic beads are coated or derivatized to specifically bind or to enhance the binding of the polymeric analyte to the magnetic beads. The environment can also be manipulated to enhance the binding of the polymeric analyte to the magnetic beads.

Another object of the present invention related to a system for detecting the presence of a polymeric analyte in a liquid sample. The system contains a rotatable magnet, preferably mounted on a motor, so that, when activated, the motor rotates the magnet to create a rotating magnetic field. A detection chamber, containing magnetic beads therein, located approximately at the center of the magnet, between its north and south poles. In use, sample is placed into the detection chamber. The motor is then activated to rotate the magnet around the detection chamber. The presence of pinwheel formations in the chamber indicates the presence of the polymeric analyte in the sample.

The method and apparatus of the present invention can be added onto already existing assays or apparatuses, especially μ-TAS, to act as a polymeric analyte detector. For example, the presence of an antibody/antigen reaction may initiate the coupling of nucleic acids and the presence/absence of the pinwheel formations determines whether the antibody/antigen binding has occurred. This is analogous to an immuno-PCR method, where instead of using PCR and fluorescent probes for the detection of nucleic acids, the pinwheel formations will be used in its place.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE PREFERRED EMBODIMENTS

The present invention is based on the novel observation that polymeric analytes, when bound to magnetic beads and in the presence a rotating magnetic field, produce unique pinwheel formations. The pinwheel effect is not seen in a static magnetic field and appears to be specific to a rotating magnetic field. "Pinwheel formation" as used herein refers to a rotating mass having a circular cross-section. The mass is made of clumps or aggregates of magnetic beads. When viewed in a still photograph (FIGS. 8-10), the pinwheel formation looks like a disc shaped object made of an aggregate of magnetic beads. However, when viewed visually or by imaging, the disc shaped object actually spins around its center axis similar to that of a spinning pinwheel. Within a detection chamber, the pinwheel formations sometimes collide together to form larger pinwheels, and sometimes collide with the wall of the chamber to break up into smaller pinwheels.

"Polymeric analyte" as used herein refers to macromolecules that are made up of repeating structural units that may or may not be identical. The polymeric analyte can include biopolymers or non-biopolymers. Biopolymers include, but are not limited to, nucleic acids (such as DNA or RNA), proteins, polypeptides, polysaccharides (such as starch, glycogen, cellulose, or chitin), and lipids.

Figure 1:
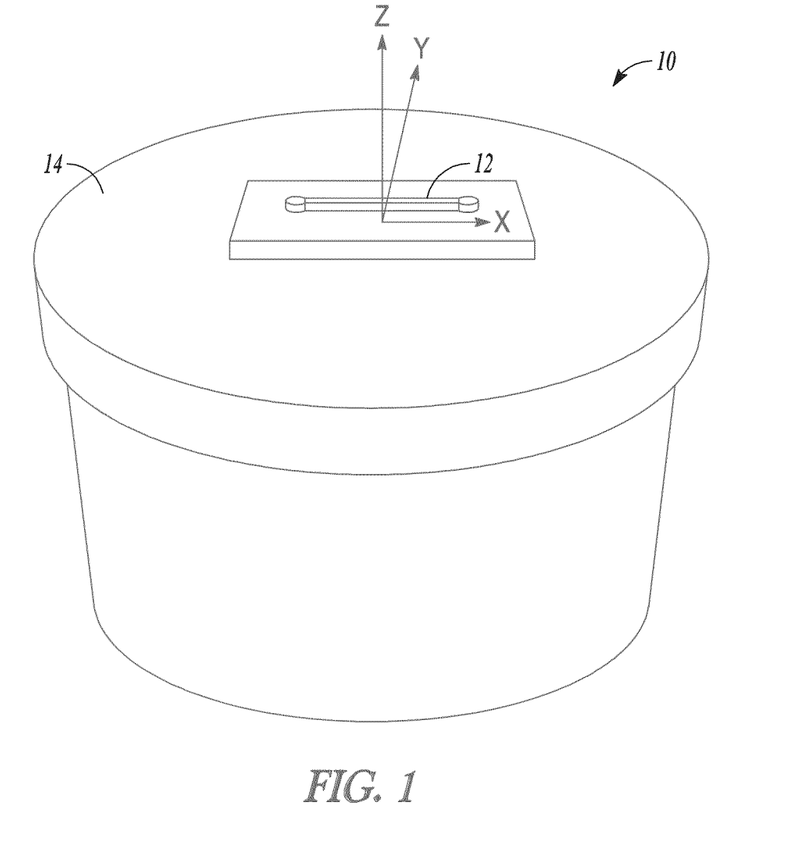
FIG. 1 shows an embodiment of the present invention where a detection chamber is placed in the center of a stir plate.
Figure 2:
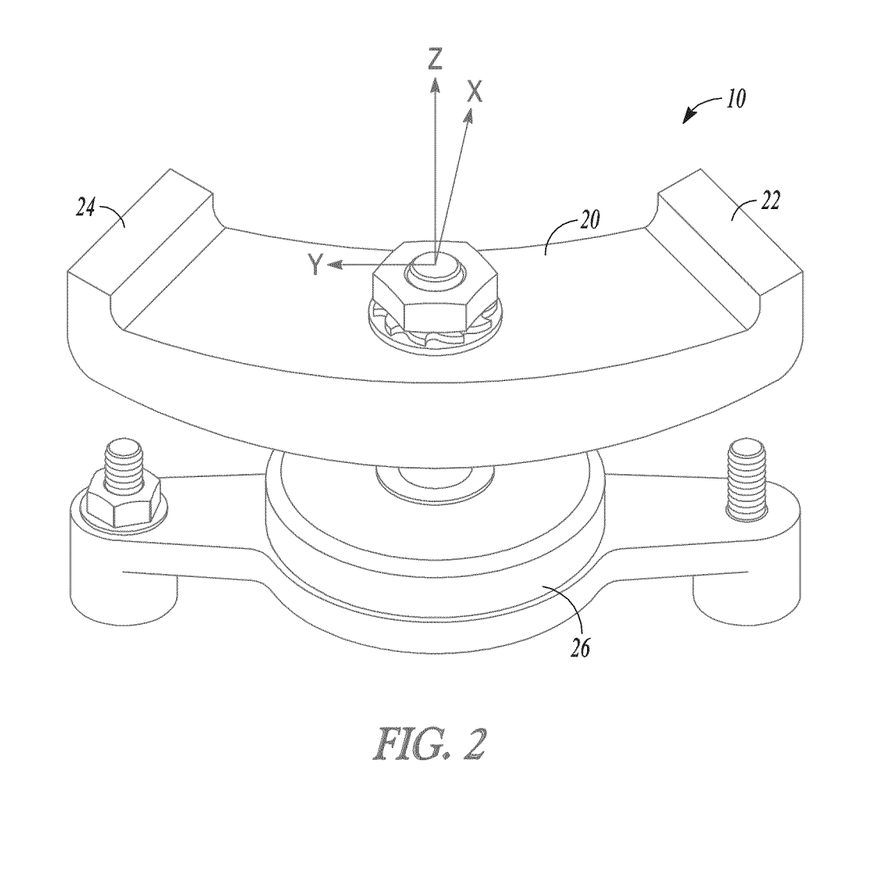
FIG. 2 shows an embodiment of a spinning magnet inside a stir plate.

The apparatus for practicing the methods of the present invention includes a rotatable magnet, preferably mounted on a motor, and a detection chamber located approximately at the center of the magnet, between its north and south pole. FIG. 1 shows an embodiment of the apparatus of the present invention containing a stir plate (10), having a rotatable magnet therein, and a detection chamber (12) placed at the center of the stir plate (10). The stir plate (10) has a top cover (14), on top of which the detection chamber (12) sits. As shown in FIG. 2, underneath to top cover (14) sits a magnet (20) having a north pole (22) and a south pole (24). The x, y, and z axes shown in FIGS. 1 and 2 are identical and serve as a reference for the two figures. Preferably, the magnet is a U-shaped magnet, as shown in FIG. 2, having its poles at either end of the U. Although this is a preferred configuration, other magnet shapes are also appropriate for the present invention, e.g. I-shape or semicircular shape magnets. The magnet is preferably mounted on a motor (24) that is capable of rotating the magnet (20) around its center axis (z). Although FIGS. 1 and 2 show the magnet (20) located directly below the detection chamber (12), this configuration is not necessary to practice the invention as long as the detection chamber is located approximately between the two poles of the magnet. The magnetic field can be positioned either parallel, orthogonal or at any angle to the detection chamber. The beads move in a defined form, where they form a pinwheel structure and spin in a distinct direction correlating to the directional rotating of the magnetic field. Although a rotatable magnet is disclosed herein, it can be replaced with other devices that can produce a rotating magnetic field. Such devices may be an electromagnet or electronic circuitry that can produce a rotating magnetic field similar to that produced by the rotating magnet.

Figure 3:
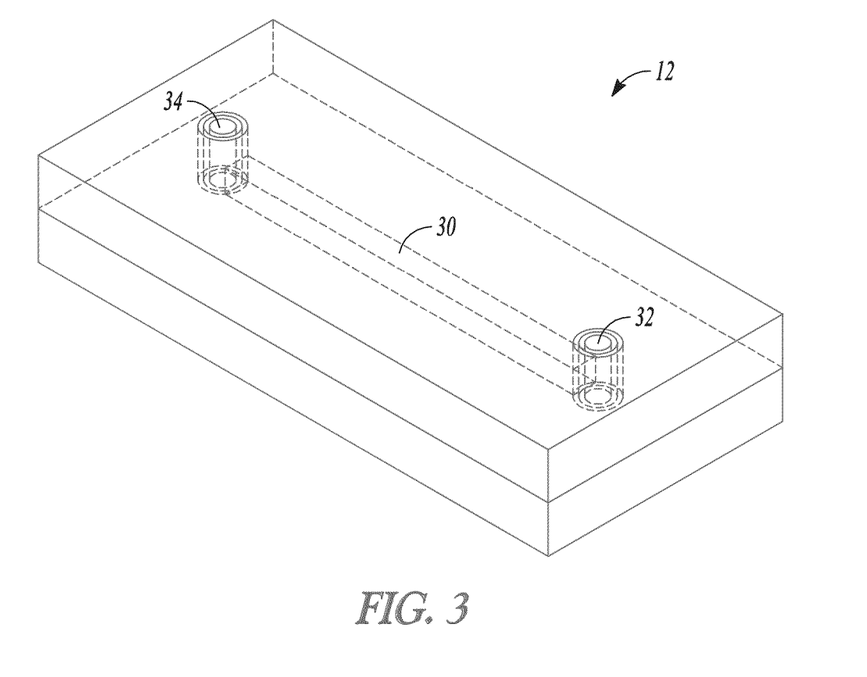
FIG. 3 shows a detection chamber.

The detection chamber (12) can be any fluid container that can be placed at approximately the center of the magnet (20) (approximately the center of the magnetic field when the magnet is rotating). Preferably, the detection chamber (12) is part or component of a microfluidic device or micro-total analysis system (μ-TAS) that are known in the prior art. Generally, a microfluidic device or μ-TAS contains at least one micro-channel. There are many formats, materials, and size scales for constructing μ-TAS. Common μ-TAS devices are disclosed in U.S. Pat. No. 6,692,700 to Handique et al.; U.S. Pat. No. 6,919,046 to O'Connor et al.; U.S. Pat. No. 6,551,841 to Wilding et al.; U.S. Pat. No. 6,630,353 to Parce et al.; U.S. Pat. No. 6,620,625 to Wolk et al.; and U.S. Pat. No. 6,517,234 to Kopf-Sill et al.; the disclosures of which are incorporated herein by reference. Typically, a μ-TAS device is made up of two or more substrates that are bonded together. Microscale components for processing fluids are disposed on a surface of one or more of the substrates. These microscale components include, but are not limited to, reaction chambers, electrophoresis modules, microchannels, fluid reservoirs, detectors, valves, or mixers. When the substrates are bonded together, the microscale components are enclosed and sandwiched between the substrates. FIG. 3 shows a simple embodiment of a detection chamber (12) that includes a microchannel (30). At both ends of the microchannel (30) are inlet (32) and outlet (34) ports for adding and removing samples from the microchannel (30). In practice, the detection chamber can be linked to other microscale components of a μ-TAS as part of an integrated system for analysis.

The detection chamber can contain magnetic beads prior to the addition of the sample or the magnetic beads can be added to the detection chamber along with the sample. The magnetic beads of the present invention preferably contain a surface that is derivatized or coated with a substance that binds or enhance the binding of the polymeric analyte to the magnetic beads. Some coatings or derivatizations known in the art include, but are not limited to, amine-based charge switch, boronic acid, silanization, reverse phase, oligonucleotide, lectin, antibody-antigen, and avidin-biotin. For example, for the detection of nucleic acid, the magnetic beads can be silica coated to specifically bind nucleic acids when exposed to a high ionic strength, chaotropic buffer. A bead could also be coated with positively charged amines or oligomers for binding with nucleic acids. For oligomers, it is preferred that they have less than about 50 bases, more preferably 5-50 bases, and most preferably 5-30 bases, so that pinwheel formations do not form without binding with a much longer nucleic acid.

To bind carbohydrates, the magnetic beads can contain a boronic acid-modified surface. Boronic acid bonds covalently and specifically to -cis dialcohols, a moity common in certain carbohydrates including glucose.

To bind lipids, the magnetic beads can be modified with hydrophobic groups, such as benzyl groups, alkanes of various lengths (6-20), or vinyl groups. The lipids are bound to the beads by hydrophobic forces.

To bind proteins, the magnetic beads can contain a protein modified surface. For example, the surface of the beads can be coated with an antibody specific for the protein of interest. For general protein detection, the bead surface can be coated with avidin or biotin and the protein of interest can be derivatized with biotin or avidin. The avidin-biotin binding thus allows the protein to bind to the beads.

In addition to derivatization or coating of the magnetic beads, the physical environment where the polymeric analyte comes into contact with the magnetic beads can also be manipulate to allow the beads to specifically bind or to enhance the binding of the magnetic beads to the polymeric analyte. For example, a silica coated bead can be manipulated to specifically bind nucleic acid, carbohydrate, or protein depending on the condition used: binding of DNA occurs in chaotropic salt solution, binding of positively charged carbohydrates occurs in low ionic strength solutions, and binding of proteins occurs under denaturing conditions (in the presence of urea, heat, etc.).

Depending on the concentration of polymeric analyte to be detected, the number of beads in the channel preferably be about 100 to about $10^8$, more preferably about $10^4$-$10^7$. The higher the concentration of analyte in the sample, the higher the amount of magnetic beads should be used. The magnetic beads preferably have an effective diameter of about 0.25-50 µm, preferably 5-8 µm. Preferably, the size of the beads is matched with the expected size of the nucleic acid being detected. Smaller beads form pinwheels with shorter polymer analytes. Bead size can be tuned to the specific cutoff in size needed for discrimination.

Figure 4:
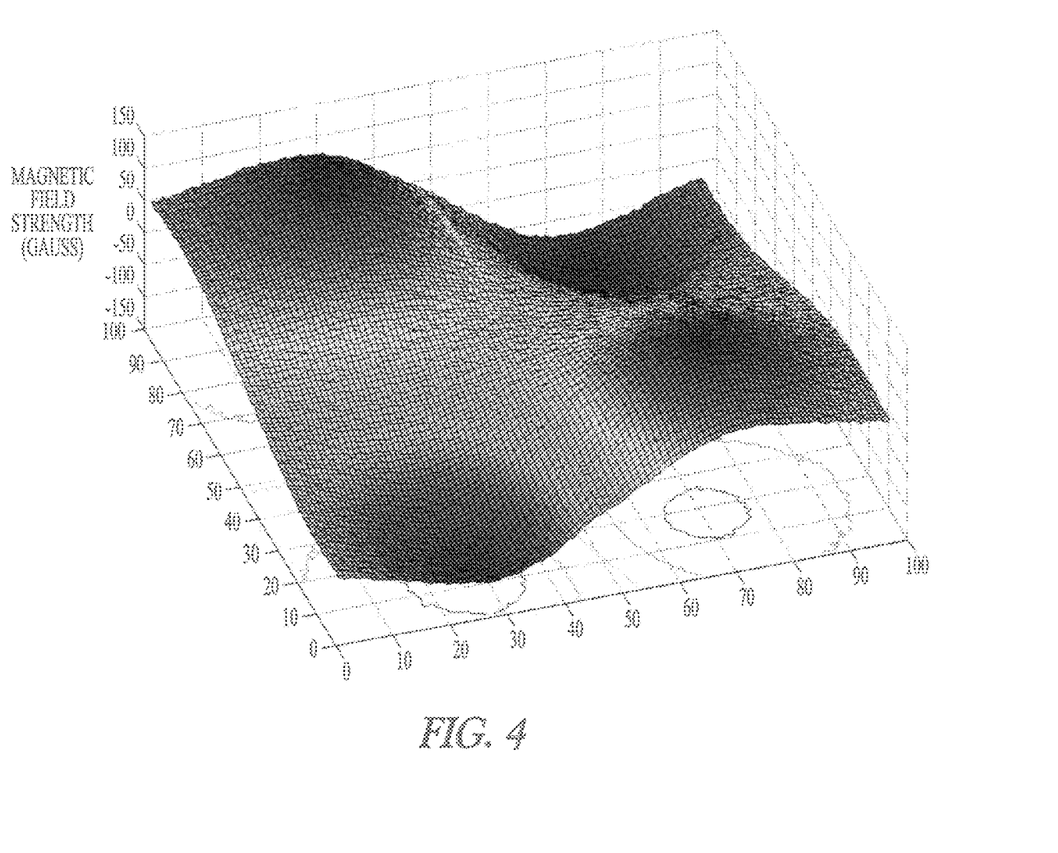
FIG. 4 shows the component of the magnetic field in the x-direction over the surface of the stir plate shown in FIG. 1.
Figure 5:
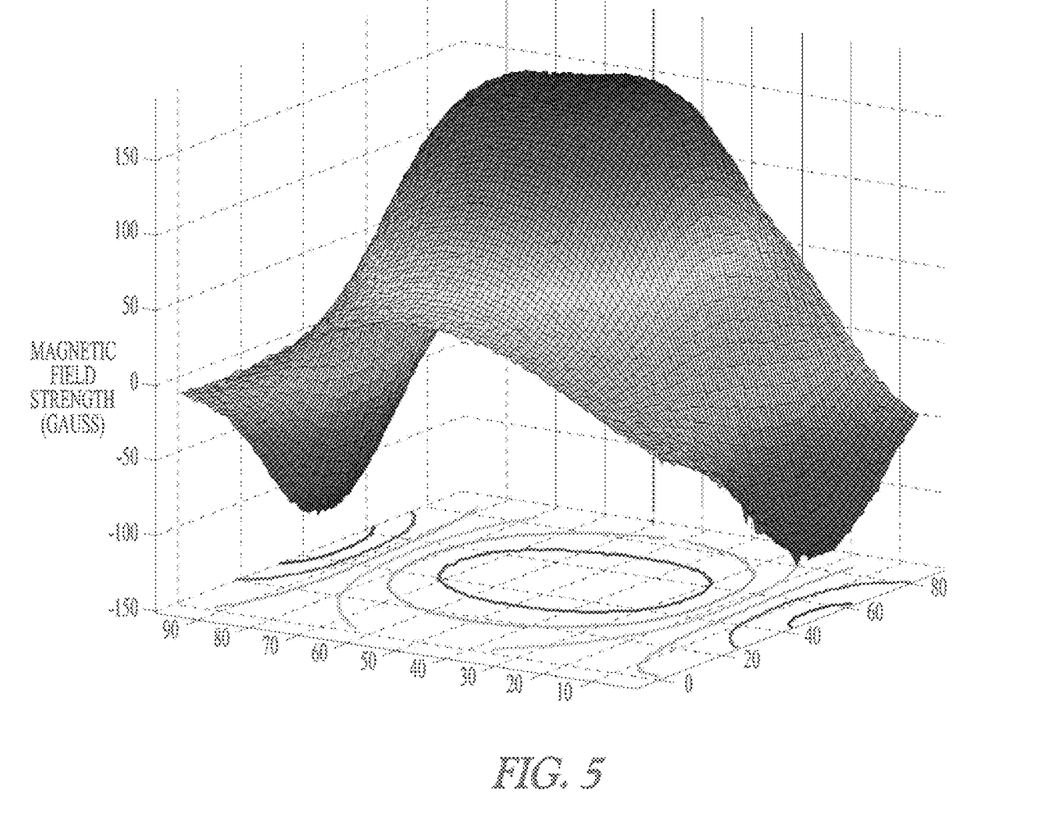
FIG. 5 shows the component of the magnetic field in the y-direction over the surface of the stir plate shown in FIG. 1.
Figure 6:
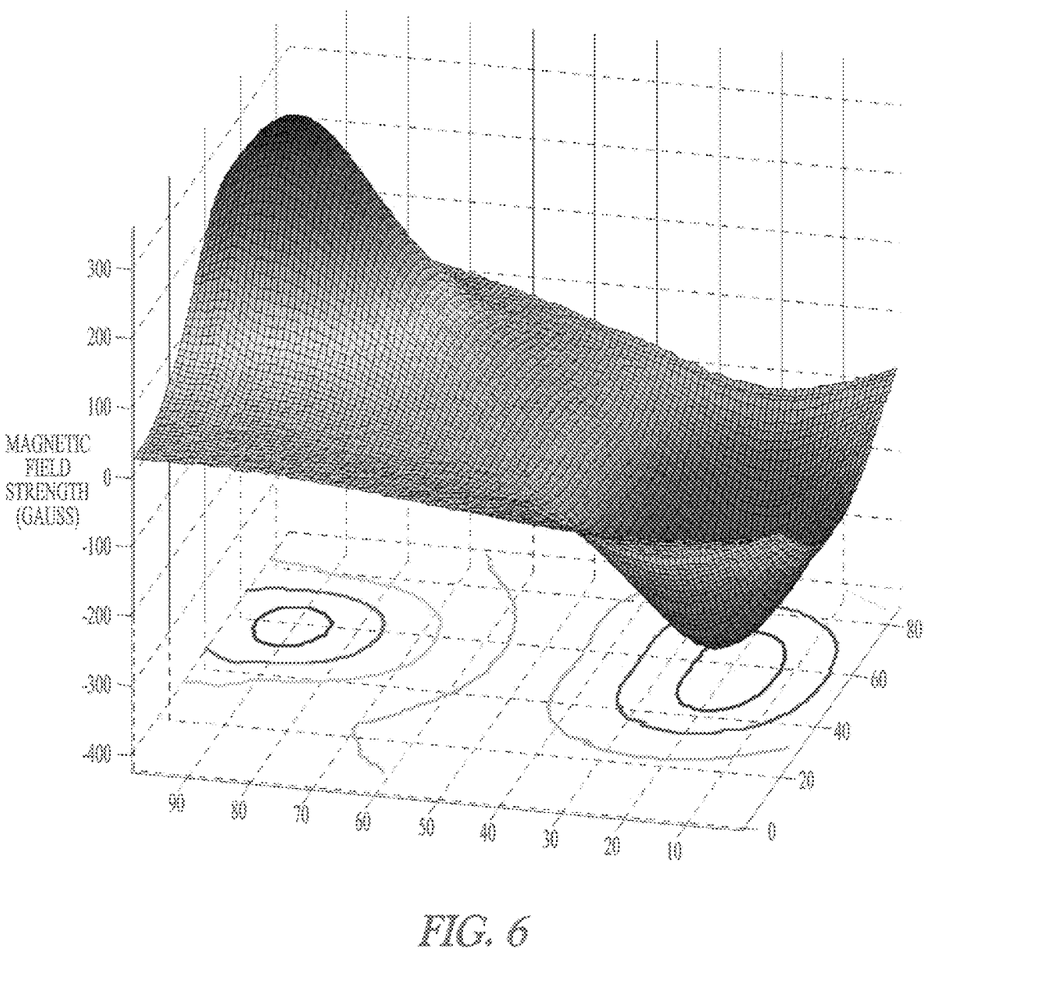
FIG. 6 shows the component of the magnetic field in the z-direction over the surface of the stir plate shown in FIG. 1.
Figure 7A:
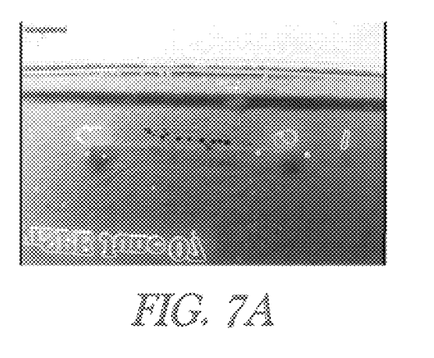
FIGS. 7*a-h* shows the screen displays of the computer program to detect pinwheel formations in a photograph of video.
Figure 7B:
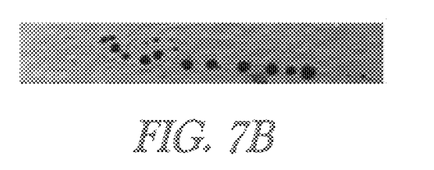
Figure 7C:
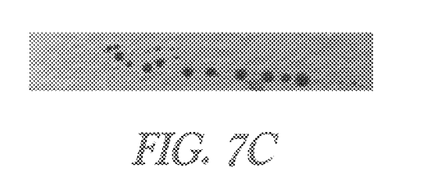
Figure 7D:
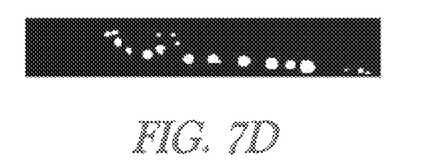
Figure 7E:
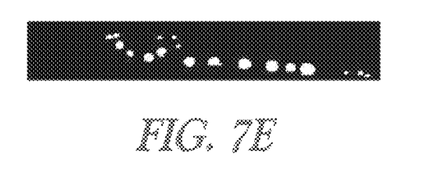
Figure 7F:
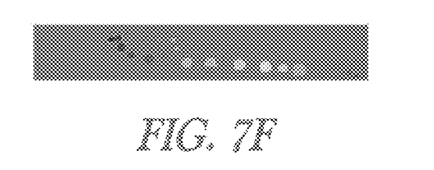
Figure 7G:
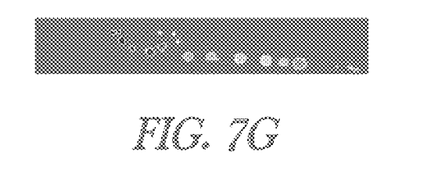
Figure 7H:
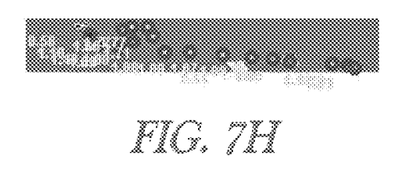

FIGS. 4-6 show the component of the magnetic field strength of the magnet in the x, y, and x axes (the x, y, and z axes are as shown in FIG. 2, with the y axis connecting the two poles of the magnet, the x axis being perpendicular to the x axis and in the rotating plane of the magnet, and the z axis perpendicular to the plane of the magnet), respectively. The components of the magnetic field in the x-axis and z-axis are essentially negligible in the center of the magnetic field and thus are likely not critical to pinwheel formation. It is preferred that the magnetic field in the y-axis has a strength of about 1-5,000 gauss, more preferably about 10-1000 gauss. Additionally, regardless of the shape of the magnet, it is preferred that the shape of the magnetic field component in the y-axis should be similar to that depicted in FIG. 5. It is preferred that this field component obtains its maximum strength at the center of rotation and is at its minimum strength at both poles of the magnet. It is preferred that this field component is maximized along the length of the magnet and abruptly drops to its minimum at the poles. It is preferred that this field component does not significantly decrease off either side of the magnet. It is also preferred that the magnetic field lines at the detection chamber are parallel to the xy-plane in which the detection chamber lies.

To detect the polymeric analyte in a sample, the sample is added to the detection chamber. The detection chamber may already contain magnetic beads therein or the magnetic beads may be added to the chamber along with the sample. Regardless of how the magnetic beads are added or the dimensions of the chamber, it is important to allow the sample and the magnetic beads to come into contact in the chamber. With the chamber locating at approximately the center of the magnet (between the two poles of the magnet), the magnet is rotated so that the chamber experiences a rotating magnetic field (the rotating magnetic field can also be effected using electronic circuitry rather than a magnet). The magnet is preferably rotated at about 10-10,000 rpm, more preferably at about 1000-3000 rpm. Observation of pinwheel formations in the channel indicates the presence of the polymeric analyte in the sample. Preferably, the average size (diameter) of the pinwheels is proportional to the concentration of nucleic acids in the sample. A calibration curve may be obtained for correlating the average size of the pinwheels to the polymeric analyte concentration. Such a calibration curve may be generated, for example, by subjecting known concentrations of the polymeric analyte to the rotating magnetic field and determining the average size of the pinwheel formations for each concentration.

The presence of pinwheel formations can be detected visually, or using optical or imaging instrumentation. One way to detect pinwheel formations is to photograph or record a video of the detection chamber. A computer program can then be used to detect the pinwheel formations in the photograph or video. An example of such a computer program is depicted in Table 1 and FIG. 7. The program initially uploads and crops the image (photograph or frames of a video) so that only the detection chamber is shown. The cropped image is then converted to gray scale. An extended minima transformation is then performed with a threshold between about 40-70 to isolate the magnetic microparticles from the background pixels. Once holes within each object are filled in, each object is then labeled, preferably with a separate RGB color. A boundary is then created around each distinct object. For each boundary, a metric $m=4\pi a/p^2$ is calculated, where a is the area of the object and p is the perimeter of the object. The metric m is a measure of the roundness of the object, for a perfect circle m=1. For each object, if m is greater than about 0.8, preferably greater than about 0.95, that object is defined as a pinwheel. A centroid is then plotted over each object having m greater than about 0.8 (a pinwheel). If a photograph is used, the number of pinwheel is then counted. If a video is used, the steps are repeated for each frame of the video and the average number of pinwheel per frame is calculated. If the number of pinwheel or average number of pinwheel per frame is greater than a set value between 0.5-10 (depending upon the polymeric analyte and bead concentration), the program returns the result that polymeric analyte is present in the sample. Table 1 and FIG. 7 show steps in the program, listings of a MATLAB® program to accomplish each step, and the computer display for some of the steps in the program. A complete listing of the MATLAB® program is presented in the appendix.

TABLE 1

| Program steps | MATLAB ® program listing | Screen display |
|---|---|---|
| 1. Open video file (from camera) and render in | [filename, pathname] = uigetfile('*.avi','Select video for analysis'); | FIG. 7a |

TABLE 1-continued

| Program steps | MATLAB ® program listing | Screen display |
|---|---|---|
| Matlab ® | complete = fullfile(pathname, filename);<br>PD = mmreader(complete);<br>get(PD) | |
| 2. Initialize variables and obtain the number of frames in the video | beadvalue = 55;<br>nframes = get(PD, 'NumberOfFrames');<br>c = 0; | |
| 3. Crop the image to only contain the microfluidic channel | crop = imcrop(read(PD, 10));<br>paste = clipboard('paste');<br>rect = str2num(paste); | FIG. 7b |
| 4. Convert image to grayscale | grayframes = rgb2gray(frame_regions); | FIG. 7c |
| 5. Perform an extended minima transform with a threshold between 40-70 to isolate the magnetic microparticles from the background pixels | beads = imextendedmin(grayframes, beadvalue); | FIG. 7d |
| 6. Fill any holes within each object | Bfill = imfill(beads, 'holes'); | FIG. 7e |
| 7. Label each object with a separate RGB color | [B,L] = bwboundaries(Bfill,'noholes');<br>    imshow(label2rgb(L, @jet, [.5 .5 .5]))<br>    hold on | FIG. 7f |
| 8. Create a boundary around each distinct object | for k = 1:length(B)<br>    boundary = B{k};<br>    plot(boundary(:,2), boundary(:,1), 'w', 'LineWidth', 1)<br>end | FIG. 7g |
| 9. Compute the area and perimeter and for each object calculate the metric $4\pi a/p^2$ | stats = regionprops(L,'Area','Centroid');<br>    threshold = 0.94;<br>    for k= 1:length(B)<br>    boundary = B{k};<br>  delta_sq = diff(boundary).^2;<br>    perimeter = sum(sqrt(sum(delta_sq,2)));<br>    area = stats(k).Area;<br>    metric = 4*pi*area/perimeter^2;<br>    metric_string = sprintf('%2.2f',metric); | |
| 10. Set a threshold of 0.94 and define an object that has a metric greater than 0.94 is a pinwheel | if metric > threshold<br>    c = c+1;<br>    centroid = stats(k). Centroid;<br>    plot(centroid(1),centroid(2), 'ro', 'LineWidth', 3);<br>end | |
| 11. Plot a centroid over each object that does satisfy this criteria, marking it as a pinwheel | text(boundary(1,2)-35,boundary(1,1)+13,metric_string, 'Color','y',..<br>    'FontSize',8,'FontWeight','bold');<br>end<br>title('Values above 0.94 and red centroid indicate pinwheel') | FIG. 7h |
| 12. Calculate the average number of pinwheels per frame | Total_pinwheels = c<br>Number_of_frames = nframes<br>Pinwheels_per_frame = c/nframes<br>if Pinwheels_per_frame > 1;<br>    hold on<br>    figure, | |
| 13. If this value is greater than a set value between 0.5-10 (depending upon the DNA and bead concentration), return to the user that DNA is present in the sample | text(0.4,0.5,'Yes','Color','g','fontsize',30, 'Fontweight','bold');<br>    title('DNA detected in sample','fontsize',18,'fontweight','bold')<br>else figure,<br>text(0.4,0.5,'No','Color','r','fontsize',30,'Fontweight','bold');<br>    title('DNA detected in sample','fontsize',18,'fontweight','bold')<br>end | |

For software based automated detection, one possible system contains at least a camera and a computer for running the computer program. In this system, the camera takes pictures or video of the detection chamber and the images from the camera is analyzed by the computer. The computer is preferably electronically connected to the camera for automatically downloading and processing the images from the camera as discussed above. The automated detection is especially efficient when the detection chamber is part of a μ-TAS where the computer can also be use to control and sense other aspects of the μ-TAS, such as temperature, fluid flow, gating, reaction monitoring, etc.

Without further description, it is believed that one of ordinary skill in the art can, using the preceding description and the following illustrative examples, make and utilize the apparatuses of the present invention and practice the methods. The following examples are given to illustrate the present invention. It should be understood that the invention is not to be limited to the specific conditions or details described in those examples.

Example 1

Figure 8:
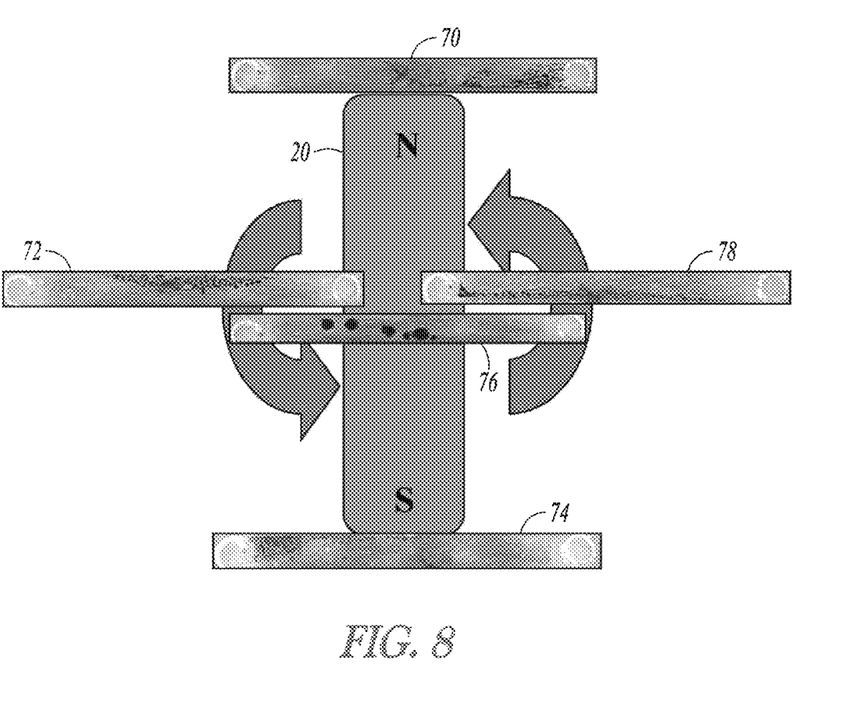
FIG. 8 shows the position of the detection chamber relative to the rotating magnet.

FIG. 8 shows the importance of the position of the detection chamber relative to the magnet (20) (N and S indicate the north and south poles of the magnet, respectively). Here, DNA and silica-coated magnetic beads are added to a microchamber (detection chamber). The detection chamber was placed at various locations (70, 72, 74, 76, and 78) relative to the magnet (20) that is rotated in the direction indicated by the arrow. From FIG. 7, it is clear that pinwheel formation is optimal at position 76, which is approximately centered between the poles of the magnet (20). The other positions do not result in pinwheel formation.

Example 2

Figure 9A:
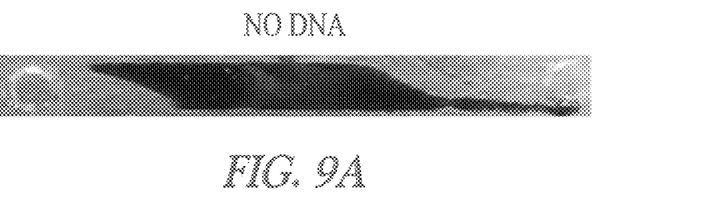
FIG. 9 shows a detection chamber having magnetic beads with and without DNA attached.
Figure 9B:
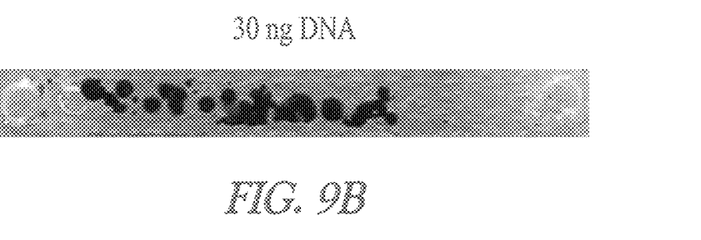
Figure 10A:
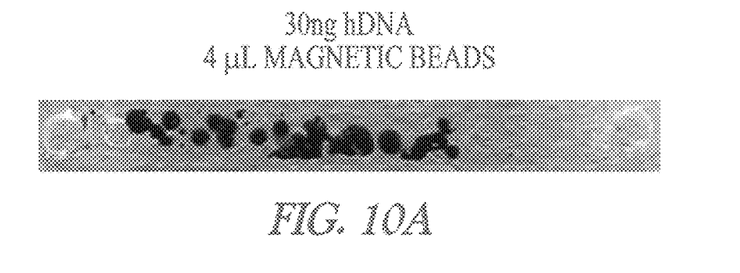
FIG. 10 shows pinwheel formations at different concentrations of DNA.
Figure 10B:
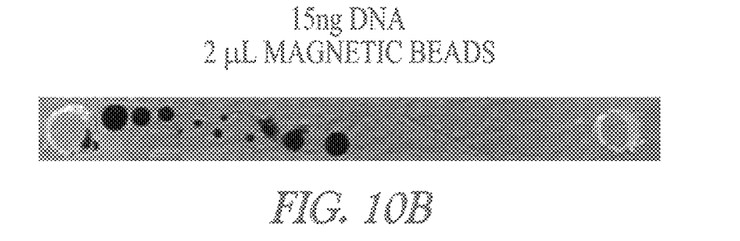
Figure 10C:
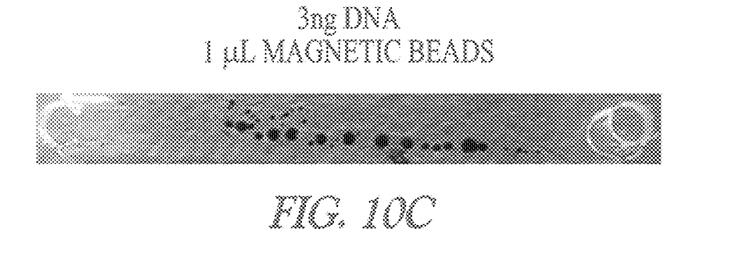
Figure 10D:
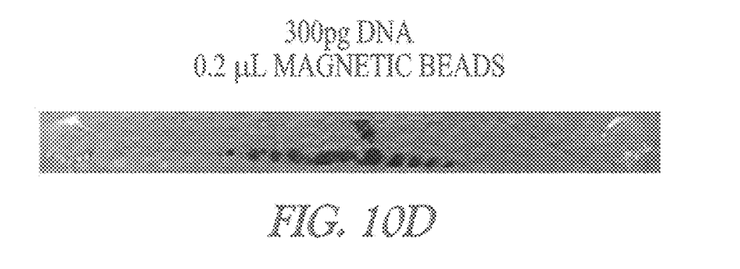
Figure 10E:
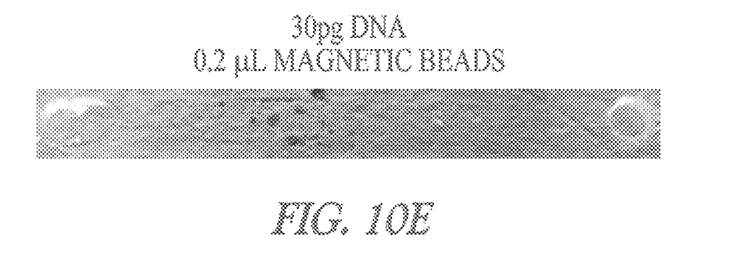

FIG. 9 shows the results using the present method on samples containing no DNA and 30 ng of human DNA. The sample containing DNA clearly shows formation of pinwheels, while the one containing no DNA shows no pinwheel formation.

FIG. 10 shows the same experiment using different DNA concentrations and bead sizes. It appears that pinwheel formations can be detected at as low as 30 pg of DNA.

Example 3

Figure 11A:
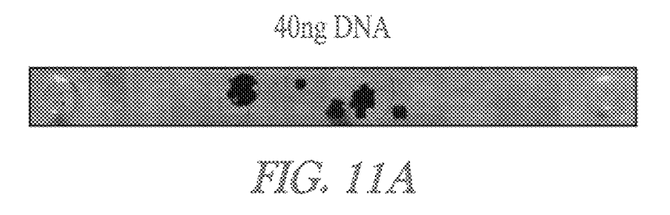
FIG. 11 shows the effect of sonication on pinwheel formation of DNA.
Figure 11B:
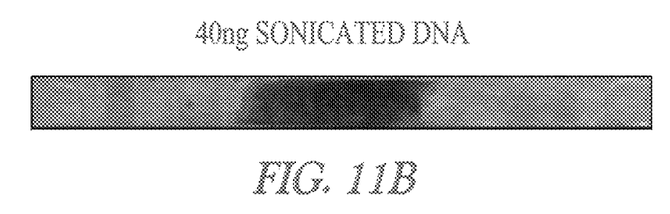
Figure 11C:
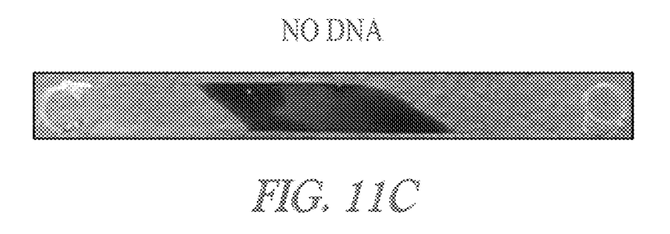
Figure 12:
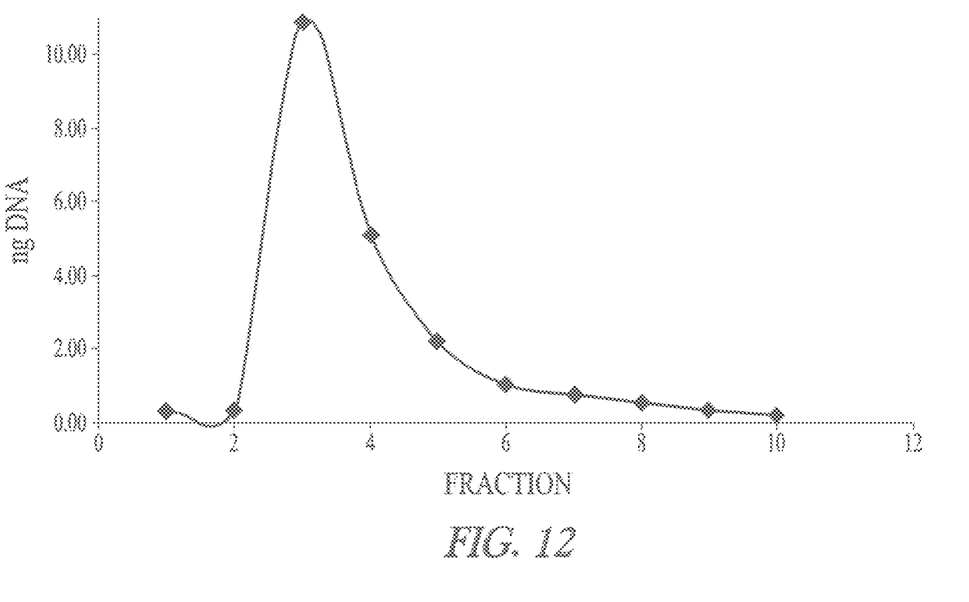
FIG. 12 shows the presence of DNA after sonication.

FIG. 11 shows the effect of sonication on human genomic DNA detection using the present method. It appears that sonicated DNA behaves as if no DNA is present. Even though DNA is still present in the sample (FIG. 12) the presence of sonicated DNA does not form pinwheels, indicating that the sonication alters the physical properties of the DNA, such as length and secondary structures, in a manner that eradicates the ability to form pinwheels and be visibly detected.

Example 4

Figure 13A:
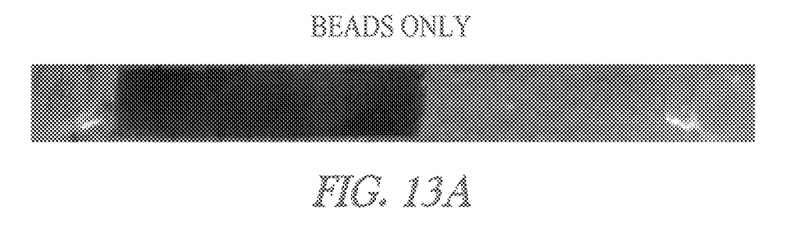
FIG. 13 shows a detection chamber having magnetic beads with and without polysaccharides attached.
Figure 13B:
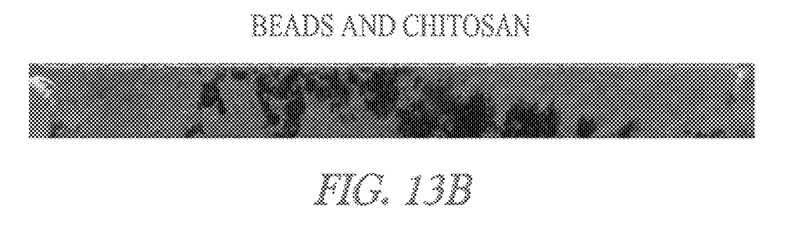

Chitosan, a cationic polysaccharide having a molecular weight of about 7 kDa, was added to Magnesil (silica coated magnetic beads) beads in a microchamber (detection chamber) in a low ionic strength solution (10 mM MES buffer, pH 5.0). The microchamber was then subjected to a rotating magnetic field. FIG. 13 shows the formation of pinwheels in the presence of the chitosan, while no pinwheel was detected in the absence of chitosan (low salt buffer only).

Although certain presently preferred embodiments of the invention have been specifically described herein, it will be apparent to those skilled in the art to which the invention pertains that variations and modifications of the various embodiments shown and described herein may be made without departing from the spirit and scope of the invention. Accordingly, it is intended that the invention be limited only to the extent required by the appended claims and the applicable rules of law.

APPENDIX

```
[filename, pathname] = uigetfile('*.avi','Select video for analysis');
complete = fullfile(pathname, filename);
PD = mmreader(complete);
```

APPENDIX-continued

```
get(PD)
beadvalue = 55;
gray = rgb2gray(read(PD,1));
nframes = get(PD, 'NumberOfFrames');
c = 0;
crop = imcrop(read(PD, 10));
paste = clipboard('paste');
rect = str2num(paste);
for count = 1:nframes
    singleframe = read(PD, count);
    frame_regions = imcrop(singleframe, rect);
    grayframes = rgb2gray(frame_regions);
    beads = imextendedmin(grayframes, beadvalue);
    Bfill = imfill(beads, 'holes');
    [B,L] = bwboundaries(Bfill,'noholes');
    imshow(label2rgb(L, @jet, [.5 .5 .5]))
    hold on
    for k= 1:length(B)
        boundary = B{k};
        plot(boundary(:,2), boundary(:,1), 'w', 'Line Width', 1)
    end
    stats = regionprops(L,'Area','Centroid');
    threshold = 0.94;
    for k= 1:length(B)
        boundary = B{k};
        delta_sq = diff(boundary).^2;
        perimeter = sum(sqrt(sum(delta_sq,2)));
        area = stats(k).Area;
        metric = 4*pi*area/perimeter^2;
        metric_string = sprintf('%2.2f',metric);
        if metric > threshold
            c = c+1;
            centroid = stats(k).Centroid;
            plot(centroid(1),centroid(2),'ro', 'Line Width', 3);
        end
        text(boundary(1,2)-35,boundary(1,1)+13,metric_string,'Color','y',...
        'FontSize',8,'FontWeight','bold');
    end
    title('Values above 0.94 and red centroid indicate pinwheel')
end
Total_pinwheels = c
Number_of_frames = nframes
Pinwheels_per_frame = c/nframes
if Pinwheels_per_frame > 1;
    hold on
    figure, text(0.4,0.5;'Yes','Color','g','fontsize',30,'Fontweight',
    'bold');
    title('DNA detected in sample','fontsize',18,'fontweight','bold')
else figure, text(0.4,0.5;'No','Color','r';'fontsize',30,'Fontweight',
'bold');
    title('DNA detected in sample','fontsize',18,'fontweight','bold')
end
```

What is claimed is:

1. A method for detecting the presence of a polymeric analyte in a sample comprising nucleic acid, protein or positively charged polysaccharide, comprising:
   (a) providing in a detection chamber a receptacle having a solution comprising the sample and an amount of magnetic beads, wherein the magnetic beads are coated or derivatized with silica, wherein the solution for detecting nucleic acid further comprises a chaotropic agent, wherein the solution for detecting positively charged polysaccharide is a solution with low ionic strength, or wherein the sample in the solution for detecting protein is subjected to denaturing conditions before placement in the receptacle;
   (b) placing the detection chamber at approximately the center of a rotating magnetic field so as to form pinwheels in the solution if the analyte is present, wherein the rotation is at 10 to 10,000 rpm, wherein pinwheel formation is specific to the presence of the binding between the nucleic acid, protein or positively charged polysaccharide and the magnetic beads; and (c) detecting the presence, amount or size of the pinwheel formations via an optical system, which formations differ from formations in the absence of the nucleic acid, protein or positively charged polysaccharide in a control sample subjected to the rotating magnetic field, wherein the presence of the pinwheel formations is indicative of the presence of the nucleic acid, protein or positively charged polysaccharide in the sample or wherein the amount or size of the pinwheel formations is indicative of the concentration of the nucleic acid, protein or positively charged polysaccharide in the sample.

2. The method of claim 1, wherein the polymeric analyte is nucleic acid.

3. The method of claim 2, wherein the nucleic acid is DNA or RNA.

4. The method of claim 1, wherein the magnetic field is generated by a U-shaped magnet.

5. The method of claim 1, wherein the magnetic beads are coated.

6. The method of claim 1, wherein the polymeric analyte is protein.

7. The method of claim 1, wherein the polymeric analyte is polysaccharide.

8. The method of claim 1, wherein the detection chamber is part of a microfluidic device.

9. The method of claim 8, wherein the device comprises a motor connected to a magnet to rotate the magnet.

10. The method of claim 1, wherein the system for detecting pinwheel formations contains a camera and a computer electronically connected to the camera for analyzing images from the camera.

11. The method of claim 10, wherein the camera is a video camera.

12. The method of claim 8, wherein the rotating magnetic field is provided by a device for generating a magnetic field which device has a magnet rotatable around its center axis or an electronic circuit.

13. A method for detecting the presence of a polymeric nucleic acid analyte in a sample comprising:
   (a) providing in a detection chamber a receptacle comprising a solution comprising a sample suspected of having a polymeric nucleic acid, a chaotropic agent and an amount of magnetic beads, wherein the magnetic beads are coated or derivatized with silica so as to enhance binding of the polymeric nucleic acid analyte;
   (b) placing the detection chamber at approximately the center of a rotating magnetic field so as to form a pinwheel if the polymeric nucleic acid analyte is present at a certain concentration in the sample relative to a control sample that lacks the polymeric nucleic acid, wherein the rotation is at 10 to 10,000 rpm; and
   (c) detecting by imaging using a system the presence or diameter of the pinwheel in the sample placed in the rotating magnetic field, wherein the presence of the pinwheel is indicative of the presence of the polymeric nucleic acid in the sample, and wherein the diameter of the pinwheel is indicative of the concentration of the polymeric nucleic acid in the sample.

14. The method of claim 13, wherein the detection chamber is part of a microfluidic device.

15. The method of claim 14, wherein the device comprises a motor connected to a magnet to rotate the magnet.

16. The method of claim 14, wherein the system for detecting pinwheel formations contains a camera and a computer electronically connected to the camera for analyzing images from the camera.

17. The method of claim 16, wherein the camera is a video camera.

18. The method of claim 13, further comprising determining the concentration of the polymeric nucleic acid in the sample.

19. The method of claim 1 wherein the amount or size of the pinwheel formations is detected.

20. The method of claim 1 wherein the pinwheel formation is detected during magnetic field rotation.

21. The method of claim 1 wherein the magnetic beads have an effective diameter of about 0.25 to 50 μm.

22. The method of claim 1 wherein the magnetic beads have an effective diameter of about 5 to 8 μm.

23. The method of claim 13 wherein the diameter of the pinwheel is detected.

* * * * *